United States Patent
Kramer et al.

(10) Patent No.: US 9,714,316 B2
(45) Date of Patent: Jul. 25, 2017

(54) POLYMER CONTAINING SILANE GROUPS

(71) Applicant: SIKA TECHNOLOGY AG, Baar (CH)

(72) Inventors: Andreas Kramer, Zürich (CH); Urs Burckhardt, Zürich (CH)

(73) Assignee: SIKA TECHNOLOGY AG, Baar (CH)

( * ) Notice: Subject to any disclaimer, the term of this patent is extended or adjusted under 35 U.S.C. 154(b) by 193 days.

(21) Appl. No.: 14/402,939

(22) PCT Filed: May 22, 2013

(86) PCT No.: PCT/EP2013/060554
§ 371 (c)(1),
(2) Date: Dec. 24, 2014

(87) PCT Pub. No.: WO2013/174892
PCT Pub. Date: Nov. 28, 2013

(65) Prior Publication Data
US 2015/0133603 A1 May 14, 2015

(30) Foreign Application Priority Data

May 23, 2012 (EP) .................... 12169151

(51) Int. Cl.
| | | |
|---|---|---|
| *C07F 7/18* | (2006.01) |
| *C08G 18/10* | (2006.01) |
| *C08G 18/48* | (2006.01) |
| *C08G 18/66* | (2006.01) |
| *C08G 18/71* | (2006.01) |
| *C08G 18/75* | (2006.01) |
| *C08G 18/83* | (2006.01) |
| *C08L 75/08* | (2006.01) |
| *C09J 175/08* | (2006.01) |

(52) U.S. Cl.
CPC .......... *C08G 18/837* (2013.01); *C07F 7/1804* (2013.01); *C07F 7/1836* (2013.01); *C07F 7/1892* (2013.01); *C08G 18/10* (2013.01); *C08G 18/4866* (2013.01); *C08G 18/6692* (2013.01); *C08G 18/718* (2013.01); *C08G 18/755* (2013.01); *C08L 75/08* (2013.01); *C09J 175/08* (2013.01); *C08G 2190/00* (2013.01)

(58) Field of Classification Search
CPC .............. C08G 18/837; C08G 18/4866; C08G 18/718; C08G 18/10; C08G 2190/00; C08G 18/6692; C08G 18/755; C07F 7/1836; C07F 7/1892; C07F 7/1804; C08L 75/08; C09J 175/08
See application file for complete search history.

(56) References Cited

U.S. PATENT DOCUMENTS

| 5,587,502 A | 12/1996 | Moren et al. |
| 2007/0041930 A1 | 2/2007 | Meder et al. |
| 2011/0034627 A1 | 2/2011 | Boudet et al. |
| 2016/0096983 A1* | 4/2016 | Burckhardt ........ C08G 18/7671 525/454 |

FOREIGN PATENT DOCUMENTS

| EP | 1452535 A1 | 9/2004 |
| EP | 1754468 A1 | 2/2007 |
| EP | 2180001 A1 | 4/2010 |
| JP | H05-186479 A | 7/1993 |
| JP | H09-296135 A | 11/1997 |
| JP | 2001-187836 A | 7/2001 |
| WO | 2005/035662 A1 | 4/2005 |
| WO | 2005035628 A1 | 4/2005 |
| WO | 2009130298 A1 | 10/2009 |

OTHER PUBLICATIONS

May 2, 2016 Office Action issued in European Patent Application No. 13 724 275.6.
De Vos et al., "Selektive Alkenoxidation mit H2O2 und einem heterogenisierten Mn-Katalysator: Epoxidierung und ein neuer Zugang zu vicinalen cis-Diolen," Angewandte Chemie, vol. 111, No. 7, 1999, pp. 1033-1036.
Aug. 20, 2013 International Search Report issued in International Application No. PCT/EP2013/060554.
Jan. 4, 2016 Office Action issued in Chinese Patent Application No. 201380026547.2.
Feb. 28, 2017 Office Action issued in Japanese Patent Application No. 2015-513167.

* cited by examiner

*Primary Examiner* — Patrick Niland
(74) *Attorney, Agent, or Firm* — Oliff PLC

(57) ABSTRACT

The invention relates to low-viscosity polymers containing silane groups, the polymers curing rapidly under the effect of moisture to form an elastic material with good heat resistance and being in particular suitable for elastic adhesives and sealants. The polymers containing silane groups are based on special hydoxysilanes which carry a secondary OH group. They are in particular obtained by reacting epoxysilanes with secondary amines.

13 Claims, No Drawings

POLYMER CONTAINING SILANE GROUPS

TECHNICAL FIELD

The invention relates to polymers containing silane groups and to their use as a component of moisture curing compositions, which are useful particularly for adhesive bonding, sealing and coating of construction and industry products.

PRIOR ART

Polymers containing silane groups, also referred to as "silane-functional polymers" or "silane-terminated polymers" or "STPs", have been used for some time successfully as binder system in moisture-curing compositions which are used, in particular, as isocyanate-free elastic adhesives, sealants and coatings in the construction and manufacturing industry. One easy route that can be implemented to obtain polymers containing silane groups, and that starts with commonly available raw materials and is thus commercially attractive, involves the reaction of aminosilanes with polyurethane polymers containing isocyanate groups, wherein finally the silane groups are bound via urea groups to the polymer. However, the polymers containing silane groups that can be obtained in this manner have a rather high viscosity, which makes it difficult to formulate compositions that have good processability and which limits their resistance to thermal stress in the cured state in the temperature range of 80° C. or higher.

Interesting properties pertaining to viscosity and heat resistance are exhibited by polymers containing silane groups, the silane groups of which are bound to the polymer via urethane groups instead of urea groups. Such polymers containing silane groups are known as reaction products of polyols with isocyanatosilanes. However, this route is of only limited interest, since isocyanatosilanes are expensive, not suitable for storage, and highly toxic. The reaction of polyurethane polymers containing isocyanate groups with hydroxysilanes would be more attractive.

U.S. Pat. No. 5,587,502 discloses silanes having hydroxyl groups, which are obtained by reacting aminosilanes with cyclic alkylene carbonates, and polymers containing silane groups derived therefrom. However, these polymers containing silane groups also have unsatisfactory heat resistance.

DESCRIPTION OF THE INVENTION

Thus, the objective of the present invention is to provide a polymer containing silane groups which has low viscosity and which cures under the effect of moisture to form an elastic material with a good heat resistance.

Surprisingly, it was found that this objective is achieved by a polymer according to claim 1. It has very low viscosity and excellent storage stability and it cures rapidly under the effect of moisture to form an elastic material with good strength, extensibility and heat resistance. The polymer can be produced surprisingly selectively by a simple process starting with polyurethane polymers containing isocyanate groups and special hydroxysilanes with a secondary OH group.

Further aspects of the invention are the subject matter of additional independent claims. Particularly preferred embodiments of the invention are the subject matter of the dependent claims.

WAYS OF IMPLEMENTING THE INVENTION

The subject matter of the invention is a polymer with end groups of formula (I), which is free of isocyanate groups,

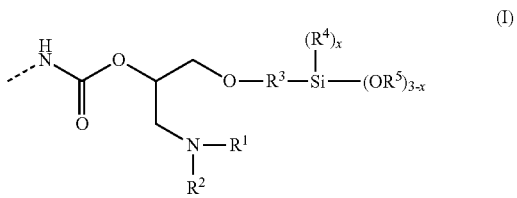

wherein $R^1$ and $R^2$ either individually each represents an alkyl radical having 1 to 12 C atoms, which optionally comprises heteroatoms in the form of ether oxygen, thioether sulfur or tertiary amine nitrogen, or together represent an alkylene radical having 2 to 12 C atoms, which optionally comprises heteroatoms in the form of ether oxygen, thioether sulfur or tertiary amine nitrogen;

$R^3$ represents a linear or branched alkylene or cycloalkylene radical having 1 to 12 C atoms, optionally with aromatic portions, and optionally with one or more heteroatoms;

$R^4$ represents an alkyl group having 1 to 6 C atoms;

$R^5$ represents an alkyl group having 1 to 10 C atoms, which optionally comprises one or more ether oxygens; and x is 0 or 1.

In the present document, the term "silane" or "organosilane" denotes compounds that, on the one hand, comprise one, usually two or three, alkoxy groups bound via Si—O bonds directly to the silicon atom, and, on the other hand, comprise at least one organic radical bound via a Si—C bond directly to the silicon atom. Accordingly, the term "silane group" denotes a silane which is bound via its organic radical.

The terms "aminosilane," "hydroxysilane," "isocyanatosilane", and the like denote organosilanes that comprise, on the organic radical, a corresponding functional group, i.e., an amino group, hydroxyl group or isocyanate group.

Substance names starting with "poly", such as polyol or polyisocyanate, denote substances that formally contain two or more of the functional groups occurring in their name per molecule.

The term "polyurethane polymer" includes all polymers that are produced by the so-called diisocyanate polyaddition process. The term "polyurethane polymer" also includes polyurethane polymers comprising isocyanate groups, obtainable by reacting polyisocyanates and polyols and which themselves represent polyisocyanates and are also often referred to as prepolymers.

In the present document, the term "molecular weight" of oligomers or polymers denotes the average molecular weight $M_n$ (number average), which is typically determined by GPC using polystyrene as a standard.

The end groups of formula (I) are silane groups. One property of the silane groups is that they hydrolyze upon contact with moisture. In this context, silanol groups (Si—OH groups) form and, due to subsequent condensation reactions, siloxane groups (Si—O—Si groups).

Preferably, $R^1$ and $R^2$ represent
either individually each an alkyl radical having 3 to 10 C atoms, which optionally comprises one or two ether oxygens,
or together an alkylene radical having 4 to 8 C atoms, which optionally comprises a heteroatom in the form of ether oxygen or thioether sulfur, and thereby, including the nitrogen atom, form a 5- or 6- or 7 ring, in particular a 5- or 6-ring.

Preferably, $R^1$ and $R^2$ represent
either individually each 2-methoxyethyl, 2-ethoxyethyl, 3-methoxypropyl, 3-ethoxypropyl, 2-(2-methoxyethoxy) ethyl, 2-octyloxyethyl, methyl, ethyl, propyl, isopropyl, butyl, isobutyl, sec-butyl or 2-ethylhexyl,
or together, including the nitrogen atom, an optionally substituted pyrrolidine, piperidine, morpholine or thiomorpholine ring.

Particularly preferably, $R^1$ and $R^2$ represent each individually 2-methoxyethyl, butyl or isopropyl, or together, including the nitrogen atom, pyrrolidine, 2-methylpiperidine, morpholine or 2,6-dimethylmorpholine. Such a polymer has particularly low viscosity and particularly good storage stability.

Most preferably, $R^1$ and $R^2$, including the nitrogen atom, represent morpholine. Such a polymer has a particularly low viscosity and particularly good storage stability, and is particularly easily accessible.

Preferably, $R^3$ represents a linear or branched alkylene radical having 1 to 6 C atoms, particularly preferably, a propylene group.

Preferably, $R^4$ represents a methyl group.

Preferably, $R^5$ represents a methyl group or an ethyl group or a hept-3,6-dioxa-1-yl group, particularly preferably a methyl group or an ethyl group.

The polymers with these preferred radicals $R^3$, $R^4$ and $R^5$ are derived from hydroxysilanes that are particularly easily accessible.

In particular, $R^5$ represents an ethyl group. These polymers are particularly storage-stable and during their curing they do not cleave off methanol, which is advantageous for toxicological reasons.

Preferably, x represents 0. Upon contact with moisture these polymers hydrolyze particularly rapidly and allow for good mechanical properties. Particularly preferably, x represents 0, and $R^5$ represents an ethyl group. These polymers having triethoxylsilane end groups are very storage-stable, cure rapidly, and have good mechanical properties in the cured state.

Preferably, the polymer having end groups of formula (I) has a molecular weight in the range from 1,000 to 30,000 g/mol, preferably 2,000 to 25,000 g/mol, particularly preferably 3,000 to 20,000 g/mol, and in particular from 4,000 to 15,000 g/mol. Such a polymer allows for good mechanical properties.

Preferably, the polymer having end groups of formula (I) comprises mostly polyoxyalkylene units, particularly preferably polyoxyethylene and/or polyoxypropylene units, in particular polyoxypropylene units. Such a polymer has a low viscosity and allows for good mechanical properties.

In particular, most of the end groups of formula (I) are bound to cycloaliphatic radicals. Such a polymer has particularly low viscosities and it is particularly light-stable.

Preferably, the polymer comprises 1 to 4, particularly preferably 1 to 3, in particular 2 or 3, most preferably 2, end groups of formula (I). Such a polymer allows for good mechanical properties, in particular a high extensibility.

Furthermore, the present invention relates to a process for producing a polymer with end groups of formula (I) by reacting at least one hydroxysilane of formula (II) with at least one polyurethane polymer containing isocyanate groups.

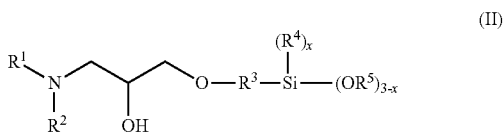

In formula (II), $R^1$, $R^2$, $R^3$, $R^4$, $R^5$ and x have the meanings as defined above.

In this reaction, the hydroxyl groups are used at least in a stoichiometric ratio, preferably, in a slightly excess, with respect to the isocyanate groups. In particular, an OH/NCO ratio from 1.0 to 1.25 is used. The reaction is preferably carried out at a temperature in the range from 20° C. to 120° C., in particular 50° C. to 100° C. Preferably, at least one catalyst is used here, in particular a bismuth(III), zinc(II) or tin(II) compound or an organotin compound.

Preferably, the hydroxysilane of formula (II) is selected from the group consisting of 1-morpholino-3-(3-(trimethoxysilyl)propoxy)propan-2-ol, 1-morpholino-3-(3-(triethoxysilyl)propoxy)propan-2-ol, 1-(2,6-dimethylmorpholino)-3-(3-(trimethoxysilyl)propoxy)propan-2-ol, 1-(2,6-dimethylmorpholino)-3-(3-(triethoxysilyl)propoxy)propan-2-ol, bis(2-methoxyethyl)amino-3-(3-(trimethoxysilyl)propoxy)propan-2-ol, bis(2-methoxyethyl)amino-3-(3-(triethoxysilyl)propoxy)propan-2-ol, 1-pyrrolidino-3-(3-(trimethoxysilyl)propoxy)propan-2-ol, 1-pyrrolidino-3-(3-(triethoxysilyl)propoxy)propan-2-ol, 1-piperidino-3-(3-(trimethoxysilyl)propoxy)propan-2-ol, 1-piperidino-3-(3-(triethoxysilyl)propoxy)propan-2-ol, 1-(2-methylpiperidino)-3-(3-(trimethoxysilyl)propoxy)propan-2-ol, 1-(2-methylpiperidino)-3-(3-(triethoxysilyl)propoxy)propan-2-ol, dibutylamino-3-(3-(trimethoxysilyl)propoxy)propan-2-ol, dibutylamino-3-(3-(triethoxysilyl)propoxy)propan-2-ol, diisopropylamino-3-(3-(trimethoxysilyl)propoxy)propan-2-ol and diisopropylamino-3-(3-(triethoxysilyl)propoxy)propan-2-ol.

The morpholino compounds are particularly preferred.
Furthermore, the triethoxysilyl compounds are particularly preferred.

A polyurethane polymer containing isocyanate groups for this reaction that is suitable for this reaction is obtained by reacting at least one polyol with at least one polyisocyanate, in particular, a diisocyanate. This reaction can occur by causing the polyol and the polyisocyanate to react by usual processes, in particular at temperatures from 50° C. to 100° C., optionally with the co-use of suitable catalysts, wherein the polyisocyanate is dosed in such a way that its isocyanate groups are present in stoichiometric excess in relation to the hydroxyl groups of the polyol. In particular, the excess of polyisocyanate is selected in such a way that, in the resulting polyurethane polymer, after the reaction of all the hydroxyl groups of the polyol, a content of free isocyanate groups of 0.1-5 wt %, preferably 0.1-2.5 wt %, particularly preferably 0.2-1 wt %, relative to the entire polymer, remains. Preferred polyurethane polymers with the mentioned content of free isocyanate groups are those obtained by reacting diisocyanates with high molecular weight diols in a NCO/OH ratio from 1.5/1 to 2.2/1, in particular 1.8/1 to 2.0/1. Optionally, the polyurethane polymer can be prepared with the co-use of plasticizers, wherein the plasticizers used contain no groups that react with isocyanates.

As polyol for the preparation of a polyurethane polymer containing isocyanate groups, the following commercial polyols or any mixtures thereof are particularly suitable:

polyoxyalkylene polyols, also referred to as polyether polyols or oligoetherols, which are polymerization products of ethylene oxide, 1,2-propylene oxide, 1,2- or 2,3-butylene oxide, oxetan, tetrahydrofuran or mixtures thereof, possibly polymerized by means of a starter molecule with two or more active hydrogen atoms, such as, for example, water, ammonia, or compounds with several OH or NH groups, such as, for example, 1,2-ethanediol, 1,2- and 1,3-propanediol, neopentyl glycol, diethylene glycol, triethylene glycol, the isomeric dipropylene glycols and tripropylene glycols, the isomeric butanediols, pentanediols, hexanediols, heptanediols, octanediols, nonanediols, decanediols, undecanediols, 1,3- and 1,4-cyclohexanedimethanol, bisphenol A, hydrogenated bisphenol A, 1,1,1-trimethylolethane, 1,1,1-trimethylolpropane, glycerol, aniline, as well as mixtures of the above-mentioned compounds. Preferable polyoxyalkylenepolyols are those having a low degree of unsaturation (measured according to ASTM D-2849-69 and indicated in milliequivalent unsaturation per gram of polyol (mEq/g)), prepared, for example, using so-called double metal cyanide complex catalysts (DMC catalysts).

Particularly suitable are polyoxyalkylenediols or polyoxyalkylenetriols, in particular polyoxyethylene- and polyoxypropylenedi- and -triols.

Also particularly suitable are so-called ethylene oxide terminated (EO end-capped) polyoxypropylenepolyols. The latter are mixed polyoxyethylene-polyoxypropylene polyols which are obtained, for example, by further alkoxylating polyoxypropylenepolyols with ethylene oxide, after the completion of the polypropoxylation reaction, and which, as a result, comprise primary hydroxyl groups.

Styrene-acrylonitrile or acrylonitrile-methyl methacrylate-grafted polyether polyols.

Polyester polyols, also referred to as oligoesterols, prepared by known processes, in particular polycondensation of hydroxycarboxylic acids or polycondensation of aliphatic and/or aromatic polycarboxylic acids with bivalent or polyvalent alcohols.

Particularly suitable polyester polyols are those that are prepared from bivalent to trivalent, and in particular bivalent, alcohols, such as, for example, ethylene glycol, diethylene glycol, propylene glycol, dipropylene glycol, neopentyl glycol, 1,4-butanediol, 1,5-pentanediol, 3-methyl-1,5-hexanediol, 1,6-hexanediol, 1,8-octanediol, 1,10-decanediol, 1,12-dodecanediol, 1,12-hydroxystearyl alcohol, 1,4-cyclohexanedimethanol, dimeric fatty acid diol (dimerdiol), hydroxypivalic acid neopentyl glycol ester, glycerol, 1,1,1-trimethylolpropane or mixtures of the above-mentioned alcohols, with organic di- or tricarboxylic acids, in particular dicarboxylic acids, or their anhydrides or esters, such as, for example, succinic acid, glutaric acid, adipic acid, trimethyladipic acid, suberic acid, azelaic acid, sebacic acid, dodecanedicarboxylic acid, maleic acid, fumaric acid, dimer fatty acid, phthalic acid, phthalic acid anhydride, isophthalic acid, terephthalic acid, dimethyl terephthalate, hexahydrophthalic acid, trimellitic acid, and trimellitic acid anhydride, or mixtures of the above-mentioned acids, as well as polyester polyols from lactones, such as, for example, from ε-caprolactone, and starters, such as the above-mentioned bivalent or trivalent alcohols.

Particularly suitable polyester polyols are polyester diols.

Polycarbonate polyols, as accessible by reacting, for example, the above-mentioned alcohols—used for the formation of the polyester polyols—with dialkyl carbonates, diaryl carbonates or phosgene.

Block copolymers carrying at least two hydroxyl groups, and comprising at least two different blocks with polyether, polyester and/or polycarbonate structure of the above-mentioned type, in particular polyether polyester polyols.

Polyacrylate and polymethacrylate polyols.

Polyhydroxy functional fats and oils, for example, natural fats and oils, in particular castor oil, or so-called oleochemical polyols prepared by chemical modification of natural fats and oils, for example, epoxy polyesters or epoxy polyethers prepared by epoxidation of unsaturated oils and subsequent ring opening with carboxylic acids or alcohols, or polyols obtained by hydroformylation and hydrogenation of unsaturated oils; or polyols obtained by degradation processes such as alcoholysis or ozonolysis and subsequent chemical linking, for example, by transesterification or dimerization of the degradation products thus obtained or derivatives thereof. Suitable degradation products of natural fats and oils are in particular fatty acids and fatty alcohols as well as fatty esters, in particular methyl esters (FAME), which can be derivatized, for example, by hydroformylation and hydrogenation to form hydroxy fatty acid esters.

Polyhydrocarbon polyols, also referred to as oligohydrocarbonols, such as, for example, polyhydroxy functional polyolefins, polyisobutylenes, polyisoprene; polyhydroxy-functional ethylene-propylene-, ethylene-butylene- or ethylene-propylene-diene copolymers, as manufactured, for example, by Kraton Polymers; polyhydroxy-functional polymers of dienes, in particular of 1,3-butadiene, which can also be prepared in particular by anionic polymerization; polyhydroxy-functional copolymers of dienes, such as 1,3-butadiene or diene mixtures and vinyl monomers, such as styrene, acrylonitrile, vinyl chloride, vinyl acetate, vinyl alcohol, isobutylene and isoprene, for example, polyhydroxy-functional acrylonitrile/butadiene copolymers, such as those that can be prepared, for example, from epoxides or amino alcohols and carboxyl-terminated acrylonitrile/butadiene copolymers (available commercially, for example, under the name Hypro® (formerly Hycar®) CTBN and CTBNX and ETBN from Nanoresins AG, Germany, or Emerald Performance Materials LLC); as well as hydrogenated polyhydroxy functional polymers or copolymers of dienes.

Preferred polyols include polyoxyalkylene polyols, polyester polyols, polycarbonate polyols and polyacrylate polyols. Polyoxyalkylene polyols are particularly preferred.

Preferred polyoxyalkylene polyols are polyoxypropylene polyols and mixed polyoxyethylene-polyoxypropylene polyols.

Preferably, the polyol has a molecular weight from 1,000 to 20,000 g/mol, particularly preferably from 2,000 to 20,000 g/mol.

Preferably, the polyol is a diol.

In addition to these polyols mentioned, small quantities of low molecular weight bivalent or polyvalent alcohols, such as, for example, 1,2-ethanediol, 1,2- and 1,3-propanediol, neopentyl glycol, diethylene glycol, triethylene glycol, isomeric dipropylene glycols and tripropylene glycols, isomeric butanediols, pentanediols, hexanediols, heptanediols, octanediols, nonanediols, decanediols, undecanediols, 1,3- and 1,4-cyclohexanedimethanol, hydrogenated bisphenol A, dimeric fatty alcohols, 1,1,1-trimethylolethane, 1,1,1-trimethylolpropane, glycerol, pentaerythritol, sugar alcohols, such as xylitol, sorbitol or mannitol, sugars, such as sucrose, other higher valency alcohols, low molecular weight alkoxylation products of the above-mentioned bivalent and polyvalent alcohols, as well as mixtures of the above-mentioned alcohols, can also be used in the manufacture of the polyurethane polymer containing isocyanate groups.

Suitable polyisocyanates for the preparation of a polyurethane polymer containing isocyanate groups are in particular the following commercial polyisocyanates or any mixtures thereof:

aliphatic isocyanates, such as, in particular, 1,4-tetramethylene diisocyanate, 2-methylpentamethylene-1,5-diisocyanate, 1,6-hexamethylene diisocyanate (HDI), 2,2,4- and 2,4,4-trimethyl-1,6-hexamethylene diisocyanate (TMDI), 1,10-decamethylene diisocyanate, 1,12-dodecamethylene diisocyanate, lysine and lysine ester diisocyanate, cyclohexane-1,3- and -1,4-diisocyanate, 1-methyl-2,4- and -2,6-diisocyanatocyclohexane and any mixtures of these isomers (HTDI or $H_6TDI$), 1-isocyanato-3,3,5-trimethyl-5-isocyanatomethyl-cyclohexane (=isophorone diisocyanate or IPDI), perhydro-2,4'- and -4,4'-diphenylmethane diisocyanate (HMDI or $H_{12}MDI$), 1,4-diisocyanato-2,2,6-trimethylcyclohexane (TMCDI), 1,3- and 1,4-bis-(isocyanatomethyl) cyclohexane, m- and p-xylylene diisocyanate (m- and p-XDI), tetramethyl-1,3- and -1,4-xylylene diisocyanate (m- and p-TMXDI), bis-(1-isocyanato-1-methylethyl)naphthaline, dimer and trimer fatty acid isocyanates, such as 3,6-bis-(9-isocyanatononyl)-4,5-di-(1-heptenyl)cyclohexene (dimeryl diisocyanate) and $\alpha,\alpha,\alpha',\alpha',\alpha'',\alpha''$-hexamethyl-1,3-5-mesitylene triisocyanate, as well as also aromatic isocyanates, such as, in particular, 2,4- and 2,6-toluylene diisocyanate and any mixtures of these isomers (TDI), 4,4'-, 2,4'- and 2,2'-diphenylmethane diisocyanate and any mixtures of these isomers (MDI), mixtures of MDI and MDI homologs (polymeric MDI or PMDI), 1,3- and 1,4-phenylene diisocyanate, 2,3,5,6-tetramethyl-1,4-diisocyanatobenzene, naphthaline-1,5-diisocyanate (NDI), 3,3'-dimethyl-4,4'-diisocyanatodiphenyl (TODI), dianisidine diisocyanate (DADI), 1,3,5-tris-(isocyanatomethyl)benzene, tris-(4-isocyanatophenyl)methane and tris-(4-isocyanatophenyl)thiophosphate, as well as oligomers and polymers of the above-mentioned isocyanates, as well as any mixtures of the above-mentioned isocyanates.

Preferred polyisocyanates are diisocyanates. IPDI, HDI, MDI and TDI, in particular IPDI, are particularly preferred. Based on IPDI, polymers with end groups of formula (I) can be produced, which have a low viscosity and which allow for good mechanical properties and a low yellowing tendency.

An additional possibility for producing a polymer with end groups of formula (I) is the reaction of at least one hydroxysilane of formula (II) with at least one diisocyanate $R^6$—$(NCO)_2$ to form an isocyanatosilane of formula (III), and the subsequent reaction of this isocyanatosilane with at least one polyol.

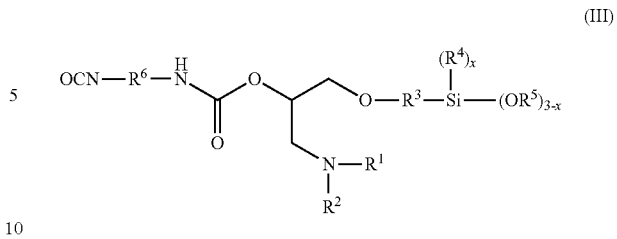

(III)

In formula (III), $R^6$ represents a bivalent hydrocarbon radical having 4 to 16 C atoms, and $R^1$, $R^2$, $R^3$, $R^4$, $R^5$ and x have the meanings as defined above.

Preferably, $R^6$ represents 1,6-hexylene, 2,2,4- and 2,4,4-trimethyl-1,6-hexylene, 1,3- and 1,4-cyclohexylene, 1,3- and 1,4-xylylene, 1,3- and 1,4-tetramethylxylylene, 4,4'- and 2,4'-substituted diphenylmethane, 2,4- and 2,6-substituted toluene and IPDI after removal of the two isocyanate groups, in particular IPDI after removal of the two isocyanate groups. These isocyanatosilanes represent easily accessible, storage-stable substances.

Thus, an additional subject matter of the present invention is an isocyanatosilane of formula (III), which represents a reaction product of at least one hydroxysilane of formula (II) with at least one diisocyanate $R^6$—$(NCO)_2$.

Suitable diisocyanate $R^6$—$(NCO)_2$ are the diisocyanates already mentioned for the preparation of a polyurethane polymer containing isocyanate groups. Particularly suitable are 1,6-hexamethylene diisocyanate, 2,2,4- and 2,4,4-trimethyl-1,6-hexamethylene diisocyanate, cyclohexane-1,3- and -1,4-diisocyanate, 1-isocyanato-3,3,5-trimethyl-5-isocyanatomethylcyclohexane, m- and p-xylylene diisocyanate, tetramethyl-1,3- and -1,4-xylylene diisocyanate, 4,4'- and 2,4'-diphenylmethane diisocyanate and 2,4- and 2,6-toluylene diisocyanate.

Among those, 1,6-hexamethylene diisocyanate, 1-isocyanato-3,3,5-trimethyl-5-isocyanatomethylcyclohexane, 4,4'- and 2,4'-diphenylmethane diisocyanate, and 2,4- and 2,6-toluylene diisocyanate are preferred.

1-Isocyanato-3,3,5-trimethyl-5-isocyanatomethylcyclohexane is particularly preferred.

Particularly preferred isocyanatosilanes of formula (III) are selected from the group consisting of 1-morpholino-3-(3-(trimethoxysilyl)propoxy)-2-propyl((5-isocyanato-1,3,3-trimethylcyclohexyl)methyl)carbamate; 1-morpholino-3-(3-(triethoxysilyl)propoxy)-2-propyl((5-isocyanato-1,3,3-trimethylcyclohexyl)methyl)carbamate; 1-(2,6-dimethylmorpholino)-3-(3-(trimethoxysilyl)propoxy)-2-propyl((5-isocyanato-1,3,3-trimethylcyclohexyl)methyl)-carbamate; 1-(2,6-dimethylmorpholino)-3-(3-(triethoxysilyl)propoxy)-2-propyl((5-isocyanato-1,3,3-trimethylcyclohexyl)methyl)carbamate; bis(2-methoxyethyl)amino-3-(3-(trimethoxysilyl)propoxy)-2-propyl((5-isocyanato-1,3,3-trimethylcyclohexyl)methyl)-carbamate; bis(2-methoxyethyl)amino-3-(3-(triethoxysilyl)propoxy)-2-propyl((5-isocyanato-1,3,3-trimethylcyclohexyl)methyl)carbamate; 1-pyrrolidino-3-(3-(trimethoxysilyl)propoxy)-2-propyl((5-isocyanato-1,3,3-trimethylcyclohexyl)methyl)carbamate; 1-pyrrolidino-3-(3-(triethoxysilyl)propoxy)-2-propyl((5-isocyanato-1,3,3-trimethylcyclohexyl)methyl)-carbamate; 1-piperidino-3-(3-(trimethoxysilyl)propoxy)-2-propyl((5-isocyanato-1,3,3-trimethylcyclohexyl)methyl)carbamate; 1-piperidino-3-(3-(triethoxysilyl)propoxy)-2-propyl ((5-isocyanato-1,3,3-trimethylcyclohexyl)methyl)carbamate; 1-(2-methylpiperidino)-3-(3-(trimethoxysilyl)propoxy)-2-propyl ((5-isocyanato-1,3,3-trimethylcyclohexyl)methyl)-carbamate; 1-(2-methylpiperidino)-3-(3-(triethoxysilyl)propoxy)-2-propyl((5-isocyanato-1,3,3-trimethylcyclohexyl)methyl) carbamate; dibutylamino-3-(3-(trimethoxysilyl)propoxy)-2-propyl((5-isocyanato-1,3,3-trimethylcyclohexyl)methyl) carbamate; dibutylamino-3-(3-(triethoxysilyl)propoxy)-2-propyl((5-isocyanato-1,3,3-trimethylcyclohexyl)methyl)-carbamate; diisopropylamino-3-(3-(trimethoxysilyl)propoxy)-2-propyl((5-isocyanato-1,3,3-trimethylcyclohexyl)methyl)carbamate and diisopropylamino-3-(3-(triethoxysilyl)propoxy)-2-propyl((5-isocyanato-1,3,3-trimethylcyclohexyl)methyl)carbamate.

The morpholino compounds are particularly preferred.

Furthermore, the triethoxysilyl compounds are particularly preferred.

In the reaction of an isocyanatosilane of formula (III) to form a polymer with end groups of formula (I), the OH groups of the polyol are preferably used approximately stoichiometrically relative to the isocyanate groups of the isocyanatosilane.

Suitable polyols for this reaction are in particular the suitable polyols already mentioned for the preparation of a polyurethane polymer containing isocyanate groups.

Polyoxyalkylene polyols, polyester polyols, polycarbonate polyols and polyacrylate polyols are preferred. Polyoxyalkylphenols are particularly preferred.

Preferred polyoxyalkylene polyols are polyoxypropylene polyols and mixed polyoxyethylene-polyoxypropylene polyols.

Preferably, the polyol has a molecular weight from 2,000 to 20,000 g/mol.

Preferably, the polyol is a diol.

Advantageously, a hydroxysilane of formula (II) can be produced by reacting at least one epoxysilane of formula (IV) with at least one amine of formula (V).

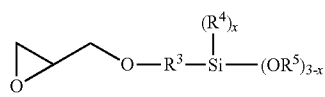

(IV)

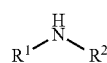

(V)

In formulas (IV) and (V), $R^1$, $R^2$, $R^3$, $R^4$, $R^5$ and x have the meanings as defined above.

This reaction is carried out preferably at temperatures in the range from 40° C. to 120° C., in particular 60° C. to 100° C. In the reaction, a catalyst can be used, in particular an imidazole, a hydroxyalkylamine, an alcohol, a phenol or an acid. The amine of formula (V) is used preferably approximately stoichiometrically relative to the epoxysilane of formula (IV). In particular, the reaction is carried out at an amine/epoxysilane ratio of 0.8 to 1.1. The reaction can be run without solvent or in a suitable solvent. Preferably, after the reaction, any volatile compounds present, in particular any solvent present, unreacted starting materials or released methanol or ethanol are removed from the reaction product by distillation.

Particularly advantageously, a hydroxysilane of formula (II) is produced by heating the reaction mixture of the epoxysilane of formula (IV) and the amine of formula (V) not above a temperature that is more than 5° C. higher than the boiling temperature of the alcohol $HOR^5$, so that any alcohol $HOR^5$ released by the self-condensation reactions remains as much as possible in the reaction mixture. Thus, in the case of methoxysilanes, the reaction is carried out particularly advantageously at a temperature below 70° C. and thus, in the case of ethoxysilanes advantageously at a temperature below 83° C. In this manner, reaction products are obtained that have a content of at least 80 wt %, preferably at least 85 wt %, in particular at least 88 wt %, hydroxysilane of formula (II). If the process is carried out at higher temperatures, then especially in the case of trialkoxysilanes, reaction products are obtained which have considerably lower contents of hydroxysilane of formula (II) due to self-condensation reactions. Such reaction products, which, in addition to other self-condensation products, typically have an increased content of cyclic silane compounds of formula (VI), are not suitable for the preparation of the described polymers with end groups of formula (I). The reaction is carried out particularly advantageously in the presence of added alcohol $HOR^5$ as solvent. Furthermore, this reaction is carried out particularly advantageously in the absence of strongly basic compounds.

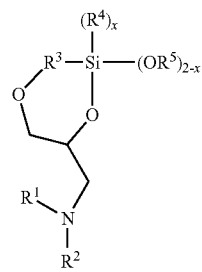

(VI)

In formula (VI), $R^1$, $R^2$, $R^3$, $R^4$, $R^5$ and x have the meanings, as defined above.

A further subject matter of the present invention is thus a reaction product obtained by reacting at least one epoxysilane of formula (IV) with at least one amine of formula (V) at a temperature which is not more than 5° C. higher than the boiling temperature of the corresponding alcohol $HOR^5$, characterized in that the reaction product has a content of hydroxysilane of formula (II) of at least 80 wt %, preferably at least 85 wt %, in particular at least 88 wt %.

This reaction is carried out preferably in the presence of added alcohol $HOR^5$. Furthermore preferably, this reaction carried out in the absence of strongly basic compounds.

Suitable epoxysilanes of formula (IV) are in particular 3-glycidoxypropyltrimethoxysilane and 3-glycidoxypropyltriethoxysilane; 3-glycidoxypropyl-triethoxysilane is preferred. These epoxysilanes result in reaction products having a particularly high content of hydroxysilane of formula (II) and particularly storage-stable hydroxysilanes of formula (II).

Suitable amines of formula (V) are in particular bis(2-methoxyethyl)amine, bis(2-ethoxyethyl)amine, bis(3-methoxypropyl)amine, bis(3-ethoxypropyl)amine, bis(2-(2-methoxyethoxy)ethyl)amine, bis(2-octyloxyethyl)amine, diethylamine, dipropylamine, diisopropylamine, dibutylamine, diisobutylamine, di-sec-butylamine, di-2-ethylhexylamine, N-methylbutylamine, N-ethylbutylamine, N-, pyrrolidine, piperidine, 2-methylpiperidine, morpholine, 2,6-dimethylmorpholine, thiomorpholine and hexamethyleneimine (=Azepan).

Among those, bis(2-methoxyethyl)amine, dibutylamine, diisopropylamine, pyrrolidine, piperidine, 2-methylpiperidine, morpholine and 2,6-dimethylmorpholine, in particular morpholine, are particularly preferred. Using these amines, reaction products are obtained that have a particularly high content of hydroxysilane of formula (II), and the hydroxysilanes of formula (II) are particularly storage-stable.

The polymer with end groups of formula (I) has good storage stability with exclusion of moisture. In the case of contact with moisture, the end groups of formula (I) hydrolyze, after which the polymer cures forming a crosslinked plastic.

Thus, the present invention also relates to a crosslinked plastic, which is obtained by reacting at least one polymer with end groups of formula (I) with moisture.

The polymer with end groups of formula (I) has advantageous properties. Its viscosity is relatively low, which is advantageous for its further processing, for example, as moisture-curing composition. It has excellent storage stability and cures under the effect of moisture rapidly to form an elastic material with good strength and extensibility and surprisingly good heat resistance. At temperatures such as 90° C., for example, the cured polymer remains elastic, while many prior art polymers containing silane groups lose all strength or even melt already after a few days.

The polymer with end groups of formula (I) is particularly suitable as component of curable compositions, in particular for the formulation of silane-functional moisture-curing compositions.

An additional subject matter of the present invention is a moisture-curing composition containing at least one polymer with end groups of formula (I) and at least one additional component.

Preferably, the moisture-curing composition according to the invention has a content of polymer with end groups of formula (I) from 5 to 90 wt %, in particular 10 to 60 wt %.

Particularly suitable additional components are catalysts, crosslinking agents, plasticizers, fillers, pigments, solvents, adhesive promoters, drying agents, rheological adjuncts and stabilizers.

Preferably, the moisture-curing composition contains at least one catalyst which accelerates the crosslinking of polymers containing silane groups. Suitable for this purpose are in particular metal catalysts and/or nitrogen-containing compounds.

Suitable metal catalysts are compounds of titanium, zirconium, aluminum and tin, in particular organotin compounds, organotitanates, organozirconates and organoaluminates, wherein these metal catalysts comprise, in particular, alkoxy groups, aminoalkoxy groups, sulfonate groups, carboxyl groups, 1,3-diketonate groups, 1,3-ketoesterate groups, dialkyl phosphate groups, and dialkyl pyrophosphate groups.

Particularly suitable organotin compounds are dialkyltin oxides, dialkyltin dichlorides, dialkyltin dicarboxylates and dialkyltin diketonates, in particular, dibutyltin oxide, dibutyltin dichloride, dibutyltin diacetate, dibutyl dilaurate, dibutyltin diacetylacetonate, dioctyltin oxide, dioctyltin dichloride, dioctyltin diacetate, dioctyltin dilaurate and dioctyltin diacetylacetonate, as well as alkyltin thioesters.

Particularly suitable organotitanates are the following:
  titanium(IV) complex compounds with two 1,3-diketonate ligands, in particular 2,4-pentane dionate (=acetylacetonate), and two alkoxide ligands;
  titanium(IV) complex compounds with two 1,3-ketoesterate ligands, in particular ethyl acetoacetate, and two alkoxide ligands;
  titanium(IV) complex compounds with one or more amino alkoxide ligands, in particular triethanolamine or 2-((2-aminoethyl)amino)ethanol, and one or more alkoxide ligands;
  titanium(IV) complex compounds with four alkoxide ligands;
  as well as more highly condensed organotitanates, in particular oligomeric titanium(IV)tetrabutoxide, also referred to as polybutyl titanate;
  wherein suitable alkoxide ligands are isobutoxy, n-butoxy, isopropoxy, ethoxy and 2-ethylhexoxy.

Most particularly suitable are bis(ethylacetoacetato)diisobutoxy titanium(IV), bis(ethylacetoacetato)diisopropoxy titanium(IV), bis(acetylacetonato)diisopropoxy titanium (IV), bis(acetylacetonato)diisobutoxy titanium(IV), tris (oxyethyl)amineisopropoxy titanium(IV), bis[tris(oxyethyl) amine]diisopropoxy titanium(IV), bis(2-ethylhexane-1,3-dioxy) titanium(IV), tris[2-((2-aminoethyl)amino)ethoxy] ethoxy titanium(IV), bis(neopentyl(diallyl)oxydiethoxy titanium(IV), titanium(IV)tetrabutoxide, tetra-(2-ethylhexyloxy)titanate, tetra-(isopropoxy)titanate and polybutyltitanate. Particularly suitable are the commercially available types Tyzor® AA, GBA, GBO, AA-75, AA-65, AA-105, DC, BEAT, BTP, TE, TnBT, KTM, TOT, TPT or IBAY (all from Du Pont/Dorf Ketal); Tytan PBT, TET, X85, TAA, ET, S2, S4 or S6 (all from TensoChema) and Ken-React® KR® TTS, 7, 9QS, 12, 26S, 33DS, 38S, 39DS, 44, 134S, 138S, 133DS, 158FS or LICA® 44 (all from Kenrich Petrochemicals).

Particularly suitable organozirconates are the commercially available types Ken-React® NZ® 38J, KZ® TPPJ, KZ® TPP, NZ® 01, 09, 12 38, 44 or 97 (all from Kenrich Petrochemicals) and Snapcure® 3020, 3030, 1020 (all from Johnson Matthey & Brandenberger).

A particularly suitable organoaluminate is the commercially available type K-Kat 5218 (from King Industries).

Nitrogen-containing compounds that are suitable as catalysts are in particular amines, such as, in particular N-ethyl diisopropylamine, N,N,N',N'-tetramethyl alkylenediamines, polyoxyalkylenamines, 1,4-diazabicyclo[2.2.2]octane; aminosilanes such as, in particular, 3-aminopropyl trimethoxysilane, 3-aminopropyl dimethoxymethylsilane, N-(2-aminoethyl)-3-aminopropyl trimethoxysilane, N-(2-aminoethyl)-3-aminopropyl methyldimethoxysilane, N-(2-aminoethyl)-N'-[3-(trimethoxysilyl)propyl]ethylenediamine as well as their analogs with ethoxy or isopropoxy instead of the methoxy groups at the silicon; amidines, such as, in particular, 1,8-diazabicyclo[5.4.0]undec-7-ene (DBU), 1,5-diazabicyclo[4.3.0]non-5-ene (DBN), 6-dibutylamino-1,8-diazabicyclo[5.4.0]undec-7-ene; guanidines such as, in particular, tetramethylguanidine, 2-guanidinobenzimidazole, acetylacetoneguanidine, 1,3-di-o-tolylguanidine, 2-tert.butyl-1,1,3,3-tetramethylguanidine; and imidazoles such as, in particular, N-(3-trimethoxysilylpropyl)-4,5-dihydroimidazole and N-(3-triethoxysilylpropyl)-4,5-dihydroimidazole.

Particularly suitable are also combinations of different catalysts, in particular combinations of at least one metal catalyst and at least one nitrogen-containing compound.

Preferred catalysts are organotin compounds, organotitanates, amines, amidines, guanidines and imidazoles. Organotitanates and amidines are particularly preferred.

Additional suitable components of the moisture-curing composition are, in particular, the following auxiliary substances and additives:
  adhesive promoters and/or crosslinking agents, in particular silanes such as the aminosilanes already mentioned as catalyst, aminosilanes with secondary amino groups, such as, in particular, N-phenyl-, N-cyclohexyl- and N-alkylaminosilanes, furthermore mercaptosilanes, epoxysilanes, (meth)acrylosilanes, anhydridosilanes, carbamatosilanes, alkylsilanes and iminosilanes, as well as oligomeric forms of these silanes, as well as adducts of primary aminosilanes with epoxysilanes or (meth)acrylosilanes or anhydridosilanes. Particularly suitable are 3-glycidoxypropyltrimethoxysilane, 3-aminopropyltrimethoxysilane, N-(2-aminoethyl)-3-aminopropyltrimethoxysilane, N-(2-aminoethyl)-N'-[3-(trimethoxysilyl)propyl]ethylenediamine, 3-mercaptopropyltrimethoxysilane, 3-ureidopropyltrimethoxysilane and the corresponding silanes with ethoxy groups instead of the methoxy groups, as well as oligomeric forms of these silanes;

plasticizers, particularly carboxylic acid esters, such as phthalates, in particular dioctyl phthalate, diisononyl phthalate or diisodecyl phthalate, adipates, in particular dioctyl adipate, azelates, sebacates, polyols, in particular polyoxyalkylene polyols or polyester polyols, glycol ethers, glycol esters, organic phosphoric and sulfonic acid esters or polybutenes;

solvents;

inorganic and organic fillers, in particular natural, ground or precipitated calcium carbonates which are optionally coated with fatty acids, in particular stearic acid, barite (heavy spar), talcs, quartz meals, quartz sand, dolomite, wollastonite, kaolin, calcined kaolins, mica (potassium aluminum silicate), molecular sieves, aluminum oxides, aluminum hydroxides, magnesium hydroxide, silicic acids including highly dispersed silicic acids from pyrolysis processes, industrially manufactured soots, graphite, metal powders such as aluminum, copper, iron, silver or steel, PVC powders or hollow beads;

fibers, in particular glass fibers, carbon fibers, metal fibers, ceramic fibers or plastic fibers such as polyamide fibers or polyethylene fibers;

dyes;

pigments, in particular titanium dioxide or iron oxides;

drying agents, in particular tetraethoxysilane, vinyltrimethoxy- or vinyltriethoxysilane and organoalkoxysilanes which have a functional group in the a position relative to the silane group, in particular N-(methyldimethoxysilylmethyl)-O-methylcarbamate, (methacryloxymethyl)silanes, methoxymethylsilanes, orthoformic acid esters, as well as calcium oxide or molecular sieves;

rheology modifiers, in particular thickeners, in particular sheet silicates such as bentonites, derivatives of castor oil, hydrogenated castor oil, polyamides, polyurethanes, urea compounds, pyrogenic silicic acids, cellulose ethers and hydrophobically modified polyoxyethylenes;

stabilizers against oxidation, heat, light and UV radiation;

natural resins, fats or oils such as colophony, shellac, linseed oil, castor oil and soybean oil;

nonreactive polymers, such as, in particular, homopolymers or copolymers of unsaturated monomers, in particular from the group comprising ethylene, propylene, butylene, isobutylene, isoprene, vinyl acetate and alkyl (meth)acrylates, in particular polyethylenes (PE), polypropylenes (PP), polyisobutylenes, ethylene vinyl acetate copolymers (EVA) and atactic poly-α-olefins (APAO);

flame-retardant substances, in particular the already mentioned fillers, aluminum hydroxide and magnesium hydroxide, as well as, in particular, organic phosphoric acid esters such as, in particular, triethyl phosphate, tricresyl phosphate, triphenyl phosphate, diphenylcresyl phosphate, isodecyl diphenyl phosphate, tris(1,3-dichloro-2-propyl)phosphate, tris(2-chloroethyl)phosphate, tris(2-ethylhexyl)phosphate, tris (chloroisopropyl)phosphate, tris(chloropropyl) phosphate, isopropylated triphenyl phosphate, mono-, bis- and tris(isopropylphenyl)phosphates of different isopropylation degree, resorcinol-bis(diphenyl phosphate), bisphenol A bis(diphenylphosphate) and ammonium polyphosphates;

surfactants, in particular crosslinking agents, leveling agents, deaerating agents or defoaming agents;

biocides, particularly algicides, fungicides or substances that inhibit fungal growth;

as well as additional substances that are usually used in moisture-curing compositions.

It may be appropriate to chemically or physically dry certain components before mixing them with the moisture-curing composition.

In addition to the polymer with end groups of formula (I), the moisture-curing composition can contain additional oligomers or polymers containing silane groups.

In a preferred embodiment, the moisture-curing composition is free of organotin compounds. This may be advantageous for ecological and/or toxicological reasons.

In an additional preferred embodiment, the moisture-curing composition does not release methanol as it cures. This may be advantageous for ecological and/or toxicological reasons.

The moisture-curing composition is preferably manufactured and stored with exclusion of moisture. Typically, the composition is storage-stable, i.e., it can be stored with exclusion of moisture in a suitable packaging or arrangement, such as, in particular, in a drum, a bag or a cartridge, for a time period from several months to one year and longer, without its application properties or its properties after the curing changing to an extent relevant to its use. Usually, the storage stability is determined by measuring the viscosity and/or the press-out force.

The moisture-curing composition can be present in the form of a single-component or in the form of a two-component composition.

In the present document, "single-component" refers to a curable composition for which all the ingredients of the composition are stored in the same container, and which is storage-stable at room temperature for a time period from several weeks to several months and curable under the effect of moisture.

In the present document, the term "two-component" denotes a composition for which the ingredients of the composition are present in two different components which are stored in separate containers and which are each individually storage-stable at room temperature. It is only shortly before or at the time of the application of the composition that the two components are mixed with one another, upon which the mixed composition cures, wherein curing occurs or is completed only due to the effect of moisture.

When applying the moisture-curing composition to at least one solid or item, the silane groups present come into contact with moisture. It is one property of the silane groups that they hydrolyze upon contact with moisture. In the process, organosilanols and, due to subsequent condensation reactions, organosiloxanes form. As a result of this reaction, the composition finally cures. This process is also referred to as crosslinking. Furthermore, silanol groups can condense with, for example, hydroxyl groups of the substrate onto which the composition is applied, as a result of which, during the curing, an excellent adhesion of the composition to the substrate can develop.

The water required for curing can originate either from the air (humidity) or the composition can be brought into contact with a water-containing component, for example, by brushing, for example, with a smoothing agent, or by spraying, or a water-containing component can be added to the composition at the time of the application, for example, in the form of a water-containing paste which is mixed in, for example, via a static mixer.

The curing occurs at varying rate depending on temperature, contact type, amount of the humidity and the presence of catalysts, if any. In the case of curing by means of humidity, first a skin forms on the surface of the composition. Accordingly, the so-called skin formation time represents a measure of the curing rate.

Thus, an additional subject matter of the present invention relates to a cured composition obtained from the curing of the moisture-curing composition under the effect of moisture.

In the cured state, the composition has elastic properties, in particular a good strength and good extensibility, good heat resistance and good adherence properties on various substrates. As a result, it is suitable for numerous uses, in particular, as fiber composite (composite), casting composition, sealant, adhesive, covering, coating or paint in construction and industry applications, for example, as an electrical insulation composition, spackling compound, caulking material, assembly adhesive, car body adhesive, plate adhesive, sandwich element adhesive, laminating adhesive, laminate adhesive, anchoring adhesive, floor covering and coating, balcony and roof coating, concrete protection coating, parking garage coating as well as protective paint against corrosion, as sealant, paint, lacquer and primer.

The moisture-curing composition is particularly suitable as adhesive and/or sealant, in particular for caulking and for elastic adhesive compounds in construction and industry applications.

Thus, an additional subject matter of the present invention is the use of the moisture-curing composition as an elastic adhesive and/or elastic sealant.

For use of the composition as a sealant, for example, for joints in building constructions and civil engineering, or for use as an adhesive for elastic adhesive bonding, for example, in vehicle construction, the composition preferably has a pasty consistency with sheer thinning properties. Such a pasty sealant or adhesive is applied to the substrate by means of an appropriate apparatus. Suitable application methods are, for example, application from commercial cartridges which are operated manually or by means of pressurized air, or from a drum or hobbock by means of a conveyance pump or an extruder, optionally by means of an application robot.

A sealant or adhesive with good application properties has a high creeping strength and short thread forming. That is, after the application it remains in the applied form, i.e., it does not flow in all directions, and, upon removing the application apparatus, it forms no or only a very short thread, so that the substrate is not soiled. An adhesive for elastic adhesive bonding, for example, in vehicle construction, is applied preferably in the form of a bead having a substantially round or triangular cross-sectional surface.

When applied as an adhesive, the composition is applied to a substrate S1 and/or a substrate S2. Thus, the adhesive can be applied to one or the other substrate or to both substrates. Subsequently, the parts to be adhesively bonded are joined together, upon which the adhesive cures by contact with moisture. Here one must ensure that the joining together of the parts occurs within the so-called open time, in order to ensure that the two joined parts are adhesively bonded to one another in a reliable manner.

When applied as a sealant, the composition is applied between the substrates S1 and S2, and subsequently curing of the composition occurs upon contact with moisture. Usually the sealant is pressed into a joint.

In both applications, substrate S1 may be the same as or different from substrate S2.

Suitable substrates S1 or S2 are in particular
glass, glass ceramic, concrete, mortar, brick, tile, plaster and natural rock such as granite or marble;
metals and alloys, such as aluminum, iron, steel and non-ferrous metals as well as surface finished metals and alloys, such as zinc coated or chromium coated metals;
leather, textiles, paper, wood, with resins, for example, phenol, melamine or epoxide resins, bonded wood materials, resin-textile composites and other so-called polymer composites;
plastics, such as polyvinyl chloride (hard and soft PVC), acrcylonitrile-butadiene-styrene copolymers (ABS), polycarbonate (PC), polyamide (PA), polyesters, poly (methyl methacrylate) (PMMA), polyesters, epoxide resins, polyurethanes (PUR), polyoxymethylene (POM), polyolefins (PO), polyethylene (PE) or polypropylene (PP), ethylene/propylene copolymers (EPM) and ethylene/propylene/diene terpolymers (EPDM), wherein preferably the plastics can be surface-treated by plasma, corona or flames;
fiber-reinforced plastics, such as carbon fiber-reinforced plastics (CFP), glass fiber reinforced plastics (GFP) and sheet molding compounds (SMC);
coated substrates, such as powder-coated metals or alloys;
paints and lacquers, in particular car top-coat lacquers.

If needed, the substrates can be pretreated prior to the application of the adhesive or sealant. Such pre-treatments include in particular physical and/or chemical cleaning processes, for example, grinding, sandblasting, brushing or the like, or treatment with cleaning agents or solvents, or the application of an adhesive promoter, an adhesive promoter solution or a primer.

After the adhesive bonding or sealing of the substrates S1 and S2 by means of a composition according to the invention, an adhesively bonded or sealed item is obtained. Such an item can be a building, in particular a structure built by building construction or civil engineering, or a transport means, for example a water or land vehicle, in particular a car, a bus, a truck, a train or a ship, or an add-on part thereof.

EXAMPLES

Exemplary embodiments are provided below, which are intended to further explain the invention described above. Of course, the invention is not limited to these exemplary embodiments described below.

"Standard atmospheric conditions" refers to a temperature of 23±1° C. and a relative humidity of 50±5%. "SAC" represents "standard atmospheric conditions".

Viscosities were determined on a thermostated cone-plate viscosimeter Rheotec RC30 (cone diameter 50 mm, cone angle 1°, cone tip-plate distance 0.05 mm, shear rate 10-100 $s^{-1}$) at a temperature of 20° C.

1. Preparation of Hydroxysilanes
Reaction Product R-1:

In a round-bottom flask, 22.27 g (80 mmol) of 3-glycidoxypropyltriethoxysilane (Dynasylan® GLYEO from Evonik Degussa), 8.36 g (96 mmol) of morpholine and 3.50 g of anhydrous ethanol were stirred under a nitrogen atmosphere for approximately 4 h at 80° C., until no further reaction progress was observed by gas chromatography. The crude product was subjected to an post-treatment for 30 minutes at 80° C. and approximately 2 mbar. A liquid product with a theoretical OH equivalent weight of 365.5 g was obtained. The reaction product had a 1-morpholino-3-(3-(triethoxysilyl)propoxy)propan-2-ol content of 94 wt % and a content of cyclic silane compound according to formula (VI) of 1 wt % (determined by gas chromatography).

Reaction Product R-2:

Prepared like reaction product R-1, except that, instead of morpholine, 8.17 g of piperidine were used. A liquid product with a theoretical OH equivalent weight of 363.6 g was obtained. The reaction product had a 1-piperidino-3-(3-(triethoxysilyl)propoxy)propan-2-ol content of 95 wt % and a content of cyclic silane compound according to formula (VI) of 1 wt % (determined by gas chromatography).

Reaction Product R-3:

Prepared like reaction product R-1, except that, instead of morpholine, 12.78 g of bis(2-methoxyethyl)amine are used. A liquid product with a theoretical OH-equivalent weight of 411.6 g was obtained. The reaction product had a bis(2-methoxyethyl)amino-3-(3-(triethoxysilyl)propoxy)propan-2-ol content of 89 wt % and a content of cyclic silane compound according to formula (VI) of 2 wt % (determined by gas chromatography).

Reaction Product R-4:

Prepared like reaction product R-1 was prepared, except that, instead of morpholine, 9.52 g of 2-methylpiperidine were used. A liquid product with a theoretical OH equivalent weight of 377.6 g was obtained. The reaction product had a 1-(2-methylpiperidino)-3-(3-(triethoxysilyl)propoxy)propan-2-ol content of 93 wt % and a content of cyclic silane compound according to formula (VI) of 1.5 wt % (determined by gas chromatography).

Reaction Product R-5: (Comparison)

20.0 g (90.4 mmol) of 3-aminopropyltriethoxysilane and 9.5 g (93.1 mmol) of 1,2-propylene carbonate were reacted analogously to Example 1 in U.S. Pat. No. 5,587,502. A liquid product with a theoretical OH equivalent weight of 323.5 was obtained.

2. Preparation of Polymers Containing Silane Groups
Polymers SP-1 to SP-4 and Comparison Polymer SP-5

For each polymer, 100 parts by weight (PW) Polymer-1 were mixed with the reaction product indicated in Table 1 in the indicated quantity. This mixture was stirred under a nitrogen atmosphere at 90° C. until no further isocyanate groups were detectable by IR spectroscopy (approximately 2 hours). Subsequently, the reaction mixture was cooled and stored with exclusion of moisture.

The properties of the polymers containing silane groups are indicated in Table 1.

Polymer-1 was produced by mixing under a nitrogen atmosphere 720 g of polyol Acclaim® 12200 (Bayer Material Science; low monol polyoxypropylenediol; OH number 11.0 mg KOH/g; water content approximately 0.02 wt %), 34.5 g of isophorone diisocyanate (Vestanat® IPDI, Evonik Degussa), 80.0 g of diisodecyl phthalate and 0.2 g dibutyltin dilaurate, heating under continuous stirring to 90° C., and maintaining at this temperature until the titrimetrically determined content of free isocyanate groups had reached a value of 0.73 wt %. The product was cooled to room temperature and stored with exclusion of moisture.

TABLE 1

Composition and properties of the polymers containing silane groups SP-1 to SP-4 and of the Comparison Polymer SP-5.

| Polymer | SP-1 | SP-2 | SP-3 | SP-4 | SP-5 (Comparison) |
|---|---|---|---|---|---|
| Polymer-1 | 100.0 | 100.0 | 100.0 | 100.0 | 100.0 |
| Reaction product (Type, Quantity) | R-1, 6.88 | R-2, 6.84 | R-3, 7.74 | R-4, 7.11 | R-5, 6.10 |
| Viscosity [Pa · s] | 51 | 86 | 39 | 60 | 52 |

3. Preparation of Moisture-Curing Compositions
Compositions Z-1 to Z-4 and Comparison Composition Z-5

For each composition, the ingredients indicated in Table 2 were mixed in the indicated quantities (in parts by weight) by means of a centrifugal mixer (SpeedMixer™ DAC 150, FlackTek Inc.) with moisture exclusion and stored. Each composition was tested as follows:

For the determination of the skin formation time, a few grams of the composition were applied in a layer thickness of approximately 2 mm to cardboard and, under standard atmospheric conditions, the time was determined in each case until no residues remained on the pipette after slightly tapping the surface of the composition with a pipette made of LDPE.

For the determination of the mechanical properties, the composition was poured onto a PTFE-coated foil to form a film having a thickness of 2 mm, which was stored for 2 weeks under standard atmospheric conditions, several dumbbell shaped samples having a length of 75 mm, with a bar length of 30 mm and a bar width of 4 mm, were punched from the film, and these dumbbell shaped samples were tested according to DIN EN 53504 at a traction rate of 200 mm/min to determine the tensile strength (force at break), elongation at rupture and E modulus (E modulus at 0.5-50% elongation).

The Shore A hardness was determined according to DIN 53505 on specimens cured for 14 days under standard atmospheric conditions.

These results are labelled "SAC:".

As a measure of the heat resistance, after the 2 weeks under standard atmospheric conditions, several dumbbell shaped samples and the Shore A specimen, respectively, were additionally stored for 1 week at 90° C. in convection oven, and then tested in the same manner for tensile strength, elongation at rupture and E modulus and for the Shore A hardness, respectively. These results are labelled "90° C.:".

The results are listed in Table 2.

TABLE 2

Composition and properties of the compositions according to the invention Z-1 to Z-4 and of the Comparison Composition Z-5.

| Composition | Z-1 | Z-2 | Z-3 | Z-4 | Z-5 (Comparison) |
|---|---|---|---|---|---|
| Polymer (type, quantity) | SP-1, 94.83 | SP-2, 94.83 | SP-3, 94.83 | SP-4, 94.83 | SP-5, 94.83 |
| Dynasylan ® AMEO [1] | 3.80 | 3.80 | 3.80 | 3.80 | 3.80 |
| Polycat ® DBU [2] | 0.34 | 0.34 | 0.34 | 0.34 | 0.34 |
| Tyzor ® IBAY [3] | 1.03 | 1.03 | 1.03 | 1.03 | 1.03 |
| Skin formation time [min] | 180 | 50 | 360 | 180 | 180 |

TABLE 2-continued

Composition and properties of the compositions according to the invention Z-1 to Z-4 and of the Comparison Composition Z-5.

| Composition | Z-1 | Z-2 | Z-3 | Z-4 | Z-5 (Comparison) |
|---|---|---|---|---|---|
| SAC: Shore A | 32 | 37 | 28 | 29 | 42 |
| Tensile strength [MPa] | 0.68 | 0.64 | 0.60 | 0.58 | 0.75 |
| Elongation at rupture [%] | 139 | 84 | 95 | 82 | 96 |
| E modulus [MPa] | 0.60 | 0.80 | 0.68 | 0.72 | 0.89 |
| 90° C.: Shore A | 29 | 23 | 26 | 30 | 24 [5] |
| Tensile strength [MPa] | 0.46 | 0.56 | 0.51 | 0.58 | n.m. [4] |
| Elongation at rupture [%] | 86 | 75 | 82 | 81 | n.m. [4] |
| E modulus [MPa] | 0.52 | 0.75 | 0.63 | 0.74 | n.m. [4] |

[1] 3-Aminopropyltriethoxysilane from Evonik Degussa
[2] 1,8-Diazabicyclo[5.4.0]undec-7-ene from Air Products
[3] Titanium(IV)-bis(ethylacetoacetato) complex from Du Pont/Dorf Ketal
[4] "n.m." represents "nicht messbar", the dumbbell shaped samples melted
[5] Specimen with hard surface and molten core Compositions Z-6 to Z-7

For each composition, 15.00 parts by weight (PW) of the polymer containing silane groups indicated in Table 3, 20.00 PW of diisodecyl phthalate, 2.00 PW of thixotropic paste, 1.00 PW of vinyl triethoxysilane (Dynasylan® VTEO from Evonik Degussa), 10.00 PW of precipitated coated calcium carbonate (Socal® U 1 S2 from Solvay), 50.00 PW of calcium carbonate (Omyacarb® 5 GU from Omya), 0.75 PW of 3-aminopropyltriethoxysilane (Dynasylan® AMEO from Evonik Degussa), 0.20 PW of 1,8-diazabicyclo[5.4.0] undec-7-ene (Polycat® DBU from Air Products) and 1.00 PW of titanium(IV)-bis(ethylacetoacetato) complex (Tyzor® IBAY from Du Pont/Dorf Ketal) were mixed by means of a centrifugal mixer (SpeedMixer™ DAC 150, FlackTek Inc.) with exclusion of moisture and stored. Each composition was tested as follows:

As measure for the storage stability, the viscosity was determined after storage with exclusion of moisture for 7 days under SAC ("Viscosity (SAC)") and a second time after the additional storage for 7 days at 60° C. ("Viscosity (60° C.)").

The skin formation time, tensile strength, elongation at rupture, E moduli and shore A hardnesses were determined in each case as described for composition Z-1.

The results are listed in Table 3.

The thixotropic paste was prepared by charging a vacuum mixer with 300 g of diisodecyl phthalate (Palatinol® Z, BASF) and 48 g of 4,4'-methylene diphenyl diisocyanate (Desmodur® 44 MC L, Bayer) and slightly warming, followed by slow dropwise addition of 27 g of monobutylamine under vigorous stirring. The forming paste was stirred for an additional hour under a vacuum and with cooling.

TABLE 3

Composition and properties of the compositions according to the invention Z-6 und Z-7.

| Composition | Z-6 | Z-7 |
|---|---|---|
| Polymer | SP-1 | SP-3 |
| Viscosity (SAC) [Pa · s] | 50 | 39 |
| Viscosity (60° C.) [Pa · s] | 54 | 50 |
| Skin formation time [min] | 235 | 215 |
| SAC: Shore A | 22 | 25 |
| Tensile strength [MPa] | 0.80 | 0.87 |
| Elongation at rupture [%] | 531 | 582 |
| E-Modulus [MPa] | 0.50 | 0.55 |

The invention claimed is:

1. A polymer with end groups of formula (I), which is free of isocyanate groups,

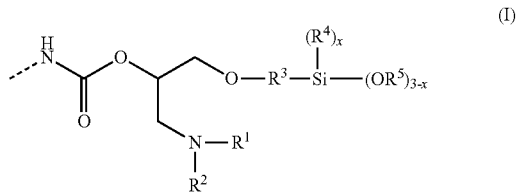

wherein
R$^1$ and R$^2$
either individually each represents an alkyl radical having 1 to 12 C atoms, which optionally comprises heteroatoms in the form of ether oxygen, thioether sulfur or tertiary amine nitrogen,
or together stand for an alkylene radical having 2 to 12 C atoms, which optionally comprises heteroatoms in the form of ether oxygen, thioether sulfur or tertiary amine nitrogen;
R$^3$ represents a linear or a branched alkylene or cycloalkylene radical having 1 to 12 C atoms, optionally with aromatic portions, and optionally with one or more heteroatoms;
R$^4$ represents an alkyl group having 1 to 6 C atoms;
R$^5$ represents an alkyl group having 1 to 10 C atoms, which optionally comprises one or more ether oxygens; and
x is 0 or 1; wherein the polymer comprises polyoxyalkylene units.

2. The polymer according to claim 1, wherein R$^1$ and R$^2$ either individually each represents an alkyl radical having 3 to 10 C atoms, which optionally comprises one or two ether oxygens, or together represent an alkylene radical having 4 to 8 C atoms, which optionally comprises a heteroatom in the form of ether oxygen or thioether sulfur, and thereby, including the nitrogen atom, form a 5- or 6- or 7 ring.

3. The polymer according to claim 1, wherein R$^3$ represents a linear or branched alkylene radical having 1 to 6 C atoms.

4. The polymer according to claim 1, wherein x is 0.

5. The polymer according to claim 1, wherein the polymer has a number average molecular weight($M_n$), as determined by GPC using polystyrene as a standard, in the range from 1,000 to 30,000 g/mol.

6. The polymer according to claim 1, wherein the end groups of formula (I) are bound to cycloaliphatic radicals.

7. The polymer according to claim 1, wherein the polymer has 1 to 4 end groups of formula (I).

8. A crosslinked plastic obtained by the reaction of at least one polymer according to claim 1 with moisture.

9. A process for producing a polymer according to claim 1, wherein at least one hydroxysilane of formula (II) is reacted with at least one polyurethane polymer containing isocyanate groups,

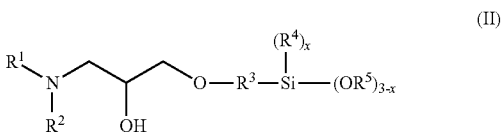

wherein
R¹ and R²
either individually each represents an alkyl radical having 1 to 12 C atoms, which optionally comprises heteroatoms in the form of ether oxygen, thioether sulfur or tertiary amine nitrogen;
or they together represent an alkylene radical having 2 to 12 C atoms, which optionally comprises heteroatoms in the form of ether oxygen, thioether sulfur or tertiary amine nitrogen;
R³ represents a linear or a branched alkylene or cycloalkylene radical having 1 to 12 C atoms, optionally with aromatic portions, and optionally with one or more heteroatoms;
R⁴ represents an alkyl group having 1 to 6 C atoms;
R⁵ represents an alkyl group having 1 to 10 C atoms, which optionally comprises one or more ether oxygens; and
x is 0 or 1.

10. An isocyanatosilane of formula (III),

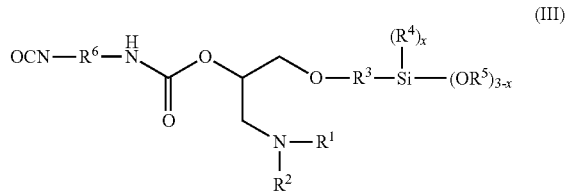

wherein
R¹ and R²
either individually each represents an alkyl radical having 1 to 12 C atoms, which optionally comprises heteroatoms in the form of ether oxygen, thioether sulfur or tertiary amine nitrogen,
or together they represent an alkylene radical having 2 to 12 C atoms, which optionally comprises heteroatoms in the form of ether oxygen, thioether sulfur or tertiary amine nitrogen;
R³ represents a linear or branched alkylene or cycloalkylene radical having 1 to 12 C atoms, optionally with aromatic portions, and optionally with one or more heteroatoms;
R⁴ represents an alkyl group having 1 to 6 C atoms;
R⁵ represents an alkyl group having 1 to 10 C atoms, which optionally comprises one or more ether oxygens;
R⁶ represents a divalent hydrocarbon radical having 4 to 16 C atoms; and
x is 0 or 1.

11. A moisture-curing composition containing at least one polymer according to claim 1 and at least one additional component.

12. A method comprising: applying the moisture-curing composition according to claim 11 as elastic adhesive and/or elastic sealant.

13. A cured composition obtained from the curing of the composition according to claim 11 with moisture.

* * * * *